(12) United States Patent
Dobos

(10) Patent No.: US 6,440,301 B1
(45) Date of Patent: Aug. 27, 2002

(54) CHROMATOGRAPHY RESIN SUPPORT

(75) Inventor: James G. Dobos, North Augusta, SC (US)

(73) Assignee: Westinghouse Savannah River Company, LLC, Aiken, SC (US)

( * ) Notice: Subject to any disclaimer, the term of this patent is extended or adjusted under 35 U.S.C. 154(b) by 40 days.

(21) Appl. No.: 09/672,600

(22) Filed: Sep. 29, 2000

(51) Int. Cl.$^7$ .............................................. B01D 15/08
(52) U.S. Cl. ..................... 210/198.2; 210/450; 210/656
(58) Field of Search ............................. 210/198.2, 232, 210/450, 456, 656; 96/101

(56) References Cited

U.S. PATENT DOCUMENTS

| | | | |
|---|---|---|---|
| 3,771,659 A | 11/1973 | Fraser ..................... | 210/198.2 |
| 4,162,977 A | 7/1979 | Guillemin et al. ........ | 210/198.2 |
| RE31,974 E | 8/1985 | Brownlee ................. | 210/198.2 |
| 4,692,243 A | 9/1987 | Porsch et al. ............ | 210/198.2 |
| 5,089,125 A * | 2/1992 | Hart ........................ | 210/198.2 |
| 5,137,628 A * | 8/1992 | Hart ........................ | 210/198.2 |
| 5,169,522 A | 12/1992 | Shalon et al. ............ | 210/198.2 |
| 5,423,982 A | 6/1995 | Jungbauer et al. ....... | 210/198.2 |
| 5,611,904 A | 3/1997 | Cole et al. ................. | 204/640 |
| 5,772,875 A | 6/1998 | Pettersson et al. ....... | 210/198.2 |
| 5,893,971 A | 4/1999 | Shalon et al. ............ | 210/198.2 |
| 5,919,361 A | 7/1999 | Moran ..................... | 210/198.2 |

\* cited by examiner

*Primary Examiner*—Ernest G. Therkorn
(74) *Attorney, Agent, or Firm*—Dority & Manning, PA

(57) ABSTRACT

An apparatus and method of using an improved chromatography resin support is disclosed. The chromatography support platform is provided by a stainless steel hollow cylinder adapted for being inserted into a chromatography column. An exterior wall of the stainless steel cylinder defines a groove for carrying therein an "O"-ring. The upper surface of the stainless steel column is covered by a fine stainless steel mesh welded to the edges of the stainless steel cylinder. When placed upon a receiving ledge defined within a chromatography column, the "O"-ring provides a fluid tight seal with the inner edge wall of the chromatography cylinder. The stainless steel mesh supports the chromatography matrix and provides a back flushable support which is economical and simple to construct.

8 Claims, 3 Drawing Sheets

CHROMATOGRAPHY RESIN SUPPORT

STATEMENT AS TO RIGHTS TO INVENTIONS MADE UNDER FEDERALLY SPONSORED RESEARCH AND DEVELOPMENT

The U.S. Government has rights in this invention pursuant to Contract No. DE-AC09-96SR18500 between Westinghouse Savannah River Company and the U.S. Department of Energy.

BACKGROUND OF THE INVENTION

Field of the Invention

This invention relates to a filter and matrix support useful in chromatography columns. More particularly, this invention relates to a filter support which may be readily provided for chromatography columns.

Chromatography is a commonly employed technique used to separate a biological or chemical material based upon the material's physical or chemical properties. For example, proteins may be separated (fractionated) using column chromatography in which a mixture of proteins in a solution are passed through a vertical column containing a porous solid matrix. The speed of passage of the proteins through the column is influenced by the interaction of the proteins with the matrix. The proteins are retarded to varying degrees based upon their interaction with the column matrix. The proteins may be separated and/or purified from a heterogeneous mixture and separately collected as the different proteins exit the column.

The column matrix may be selected to discriminate materials based upon size, shape, electrical charge, or binding affinity for a particular substrate present on the matrix materials. For instance, ion-exchange columns may be packed with small beads or resin which carry a positive or negative charge. As a result, materials passing over the column are separated according to their charge properties.

Gel-filtration columns are packed with small porous beads and are used to separate a material, such as a protein, based upon size. Smaller molecules enter successive beads and thereby take longer to migrate along the column distance while materials too large to enter the interior of the beads flow rapidly through the column.

Affinity columns may be used to separate materials by attaching specific molecules, such as an enzyme, lectin or antibody, which will selectively interact with and bind target molecules passed over the column. Upon elution from the column, a purified fraction of the released target molecules may then be collected.

Traditionally, chromatography columns are made of borosilicate glass and are commercially available in various sizes ranging from 0.7–4.8 cm I.D. Such columns typically use a polyethylene bed support which is supplied with the column. However, the standard sizes of traditional liquid chromatography columns and accessories are not compatible with other standard lab glassware supplies. Further, some bed supports use a ceramic frit to support the separation matrix and are subject to clogging, flow rate changes over time, and are difficult to clean for reuse. Accordingly there is a need within the art for liquid chromatography columns which conforms to and may make use of standard laboratory glassware supplies.

DESCRIPTION OF RELATED ART

A variety of chromatography columns and related accessories are known within the art. U.S. Pat. No. 5,893,971, incorporated herein by reference, is directed to a liquid chromatography apparatus in which a lower column end is attached to a retaining plate. Within the retaining plate, a frit holder is provided, external to the column, to provide support to the column matrix such as a resin or silica particulate.

In U.S. Pat. No. Re. 31,974, incorporated herein by reference, is directed to pressure chromatography. A multipurpose end plug is used to seal and plug the column end.

In U.S. Pat. Nos. 3,771,659 and 4,692,243, both of which are incorporated herein by reference, disclose various filter holders and support members for retaining a resinous matrix within the separation column.

Despite the wide assortment of available apparatuses and teachings present within the art, there remains room for improvement and variation within the art liquid chromatography.

SUMMARY OF THE INVENTION

It is an object of this invention to provide an apparatus which facilitates the use of standard sized and configured laboratory glassware as a chromatography column.

It is a further object of this invention to provide a support structure for retaining a chromatography resin within the interior of a glass cylinder.

It is a further object of this invention to provide a chromatography support structure to which a back pressure may be applied to packed column, thereby clearing particulate from the matrix and reestablishing an improved flow rate of the column.

It is a further and more particular object of this invention to provide a stainless steel matrix holder, the holder defining a central opening and further defining a circumferential, reduced diameter groove engaged by a gasket such as an O-ring. The installed O-ring has an outer diameter which is greater than the bushing O.D. A mesh screen covers an upper surface and top opening of the bushing. When placed inside a glass column, the bushing can be inserted into the column and placed inside a ledge defined along the interior wall of a lower end of the column. When so placed, the bushing provides a liquid-tight seal around the periphery of the column. The mesh screen provides a support structure for a chromatography resin or other matrix.

These and other objects of the invention are accomplished by a chromatography support comprising: a resin support apparatus for a chromatography column comprising: a stainless steel cylinder having an outer diameter and an inner diameter, the outer diameter being greater than a height of the stainless steel cylinder, the cylinder defining a groove in an exterior wall of the stainless steel cylinder, the groove being substantially parallel to an upper and a lower rim of the stainless steel cylinder; an "O"-ring positioned within the groove, the "O"-ring having an outer diameter greater than the outer diameter of the stainless steel cylinder; and, a stainless steel mesh welded to an upper surface of the stainless steel cylinder and covering an opening defined by the stainless steel cylinder; wherein, when said stainless steel cylinder is placed within a receiving ledge formed on an interior surface of a volumetric cylinder, the "O"-ring provides a fluid tight seal between the stainless steel cylinder and the inner wall of the graduated cylinder, the stainless steel mesh providing a support platform adapted for receiving a supply of a chromatography matrix.

Further objects of the invention are provided by a method of constructing a chromatography column comprising: supplying a glass tubing having an upper opening and a lower opening; forming a reduced inner diameter taper along an interior surface of the glass tubing; positioning a steel cylinder having an inner diameter and an outer diameter onto the taper, the steel cylinder further defining an "O"-ring positioned within a circumferential groove, the "O"-ring having an outer diameter greater than an inner diameter of the glass cylinder; attaching to an upper surface of the steel cylinder a stainless steel mesh, the mesh extending across an upper opening defined by the stainless steel cylinder; introducing a supply of a chromatography matrix material into the volumetric cylinder, the matrix being supported along a mesh carried by the steel cylinder.

DETAILED DESCRIPTION OF THE INVENTION

In describing the various figures herein, the same reference numbers are used throughout to describe the same apparatus. To avoid redundancy, detailed descriptions of much of the apparatus once described in relation to a figure is not repeated in the descriptions of subsequent figures, although such apparatus or process is labeled with the same reference numbers.

Figure 1:
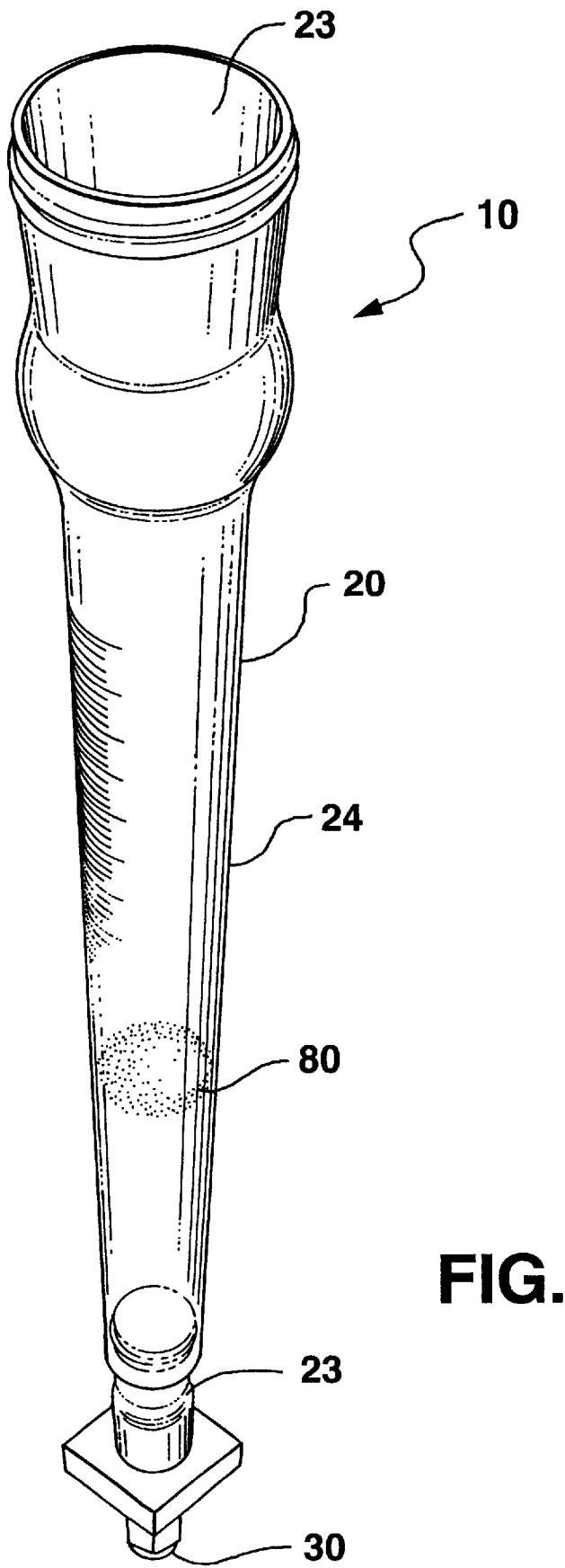
FIG. 1 depicts a perspective view of a graduated chromatography column in accordance with this invention.

In FIG. 1 an embodiment of a chromatography column 10 according to the present invention is set forth. Column 10 comprises a glass tubing or cylinder 20 having volume indicia 22 present along a mid-segment of cylinder. The mid-segment 24 of the cylinder preferably has a constant inner diameter along its length. An upper end of the cylinder may be provided with a tapered ground glass inner surface 23 for connection to a correspondingly shaped connector of a glass ware accessory.

A lower end of the cylinder (FIG. 2) defines a reduced inner diameter terminus which further defines a internal threading 26 which is adapted for engaging a similar threaded polyethylene connector 28. The connector 28 supports an O-ring 29 along the upper threaded end of the connector. A lower end of the connector is in fluid communication with a stainless steel coupling 30 such as a SWAGELOK™ coupling which is adapted for engaging a terminal end of a length of tubing. When so configured, there is an open pathway of communication between the upper column and extending through the coupling 30.

The lower end of mid-segment 24 provides an inner taper 40 of a reduced diameter wall portion of cylinder 20. As seen in reference to FIG. 2, taper 40 provides a ledge-like structure which engages a resin support platform 50. Platform 50 may be provided by a stainless steel cylinder 52 having a diameter which is greater than a height of cylinder 52. The interior wall 54 of cylinder 52 defines a uniform inner diameter of the cylinder. An upper steel cylinder wall 56 and a lower steel cylinder wall 58 provide a substantially flush horizontal surface. Upper wall surface 56 is operatively engaged by a stainless steel #200 wire mesh 60. For instance mesh 60 may be attached by spot welding the mesh 60 to the upper steel cylinder wall surface 56. The lower cylinder wall 58 may define a slight taper 62 between the interior rim of wall 58 and the interior cylinder wall 54. The taper 62 may help to facilitate seating of platform 50 onto ledge 40 as seen in FIG. 2.

An exterior wall of steel cylinder 52 defines a circumferential groove 64 which is positioned along the midpoint of the steel cylinder 52. The upper groove wall 66 and lower groove wall 68 are substantially parallel. Further, both groove walls 66 and 68 define a perpendicular plane with respect to an axis "A" of cylinder 52. The interior wall of groove 64 is normal to the respective upper and lower groove walls 66 and 68. As such, the interior groove wall defines a plane which is parallel to the plane of the interior cylinder wall 54.

A resilient O-ring 70 is placed within groove 64. O-ring 70 is circular in a radial section and has an inner diameter slightly greater then the outer diameter of interior wall 70 of groove 64. Similarly, the height of O-ring 70 is such that the upper and lower surfaces of the O-ring engage the corresponding upper and lower groove walls 66 and 68 when positioned within the groove. An outer diameter of the O-ring 70 corresponds to the inner diameter of graduated cylinder 20 and accordingly extends outwardly beyond the exterior wall of steel cylinder 52. When properly positioned, the O-ring 70 defines a fluid tight, i.e. gas and liquid, seal between the steel cylinder 52 and the interior wall 21 of glass cylinder 20. In this manner, fluids passing through the column 20 must pass through the interior of steel cylinder 52.

Figure 2:
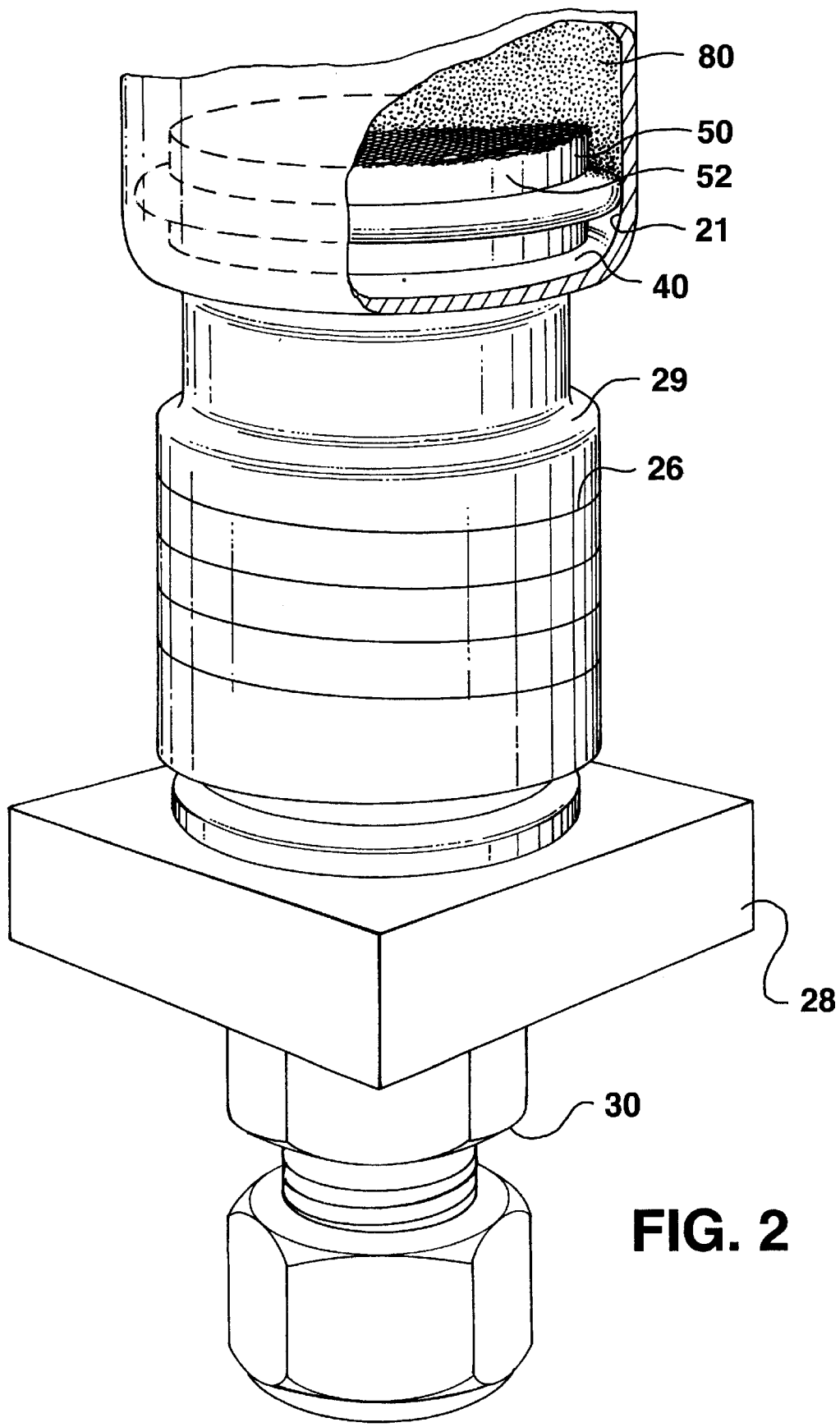
FIG. 2 depicts an enlarged view of a portion of the chromatography column of FIG. 1; and, FIG. 3 is an perspective view of the resin support structure which forms a part of the present invention.
Figure 3:
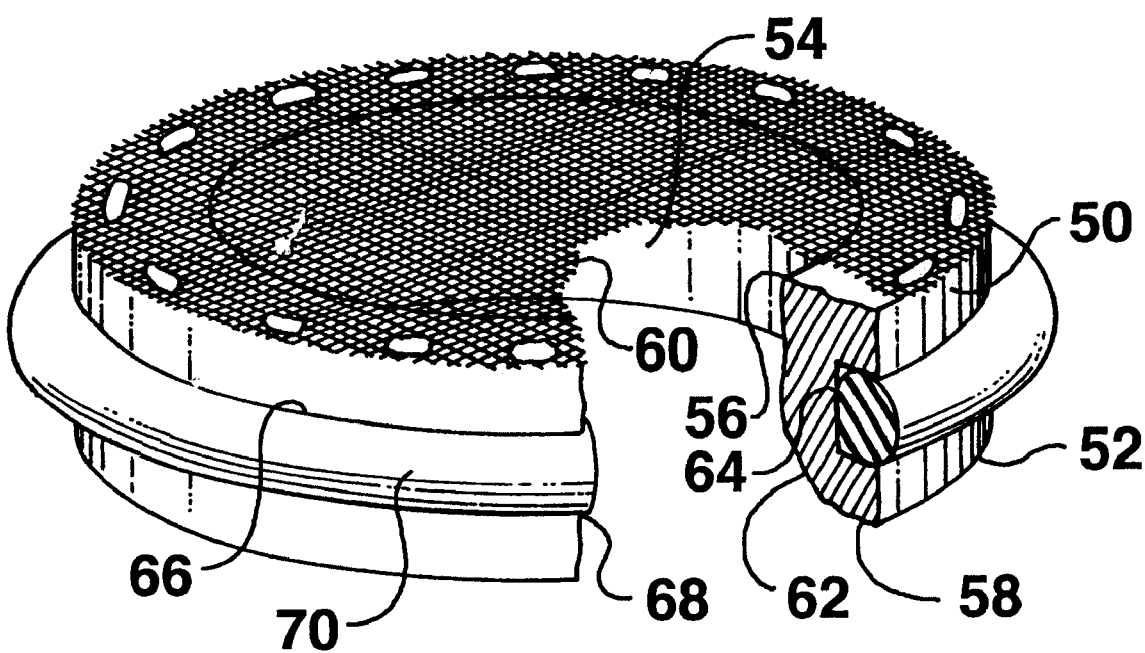

As seen in reference to FIG. 2, a desired volume of the chromatography matrix 80, such as a beaded agarose, sepharose, ceramic, or glass particulates, is supported upon the support structure 50. Where required, conventional column packing techniques may be carried out. The wire mesh 60 supports the packed matrix 80 and has a mesh sized appropriately to prevent passage of the intact matrix material.

EXAMPLE 1

By way of example and in reference to the FIGS. above, a borosilicate chromatography column 10 may be provided having a height of about 20 cm, an inner diameter along a mid-segment of 2.71 cm and an outer diameter of 3.17 cm. The matrix support cylinder has an outer diameter of about 2.40 cm, an inner diameter of about 1.70 cm and a height of about 0.69 cm. The groove 64 extends a uniform depth of about 0.35 cm from the outer cylinder wall 53. A circular piece of #200 stainless steel wire mesh is spot welded to the upper surface 56 of steel cylinder 52. The O-ring 70 may be provided from a Viton™ material, Teflon™ material, rubber, or other resilient material and has an inner diameter of about 2.00 cm, an outer diameter of about 2.65 cm, and a height of about 0.31 cm. Support 50, bearing O-ring 70, is inserted through the top of the column and positioned with lower cylinder wall 58 positioned flush against an upper surface of ledge 40. As illustrated in FIG. 2, when the matrix support is in an operative position, the upper cylinder wall 56 and wire mesh 60 are aligned with the "0" volumetric indicia. When so aligned, the chromatography column allows for accurate volumetric adjustments in measurements.

The threaded connector 28 permits, via coupling 30, the controlled elution of materials through the column. The stainless steel cylinder 52 along with "O" ring 70 provide a tight fluid impermeable seal which further prevents loss of the matrix material 80 from the graduated cylinder. The resulting support structure is easily constructed to fit a variety of sizes with respect to both inner and outer diameters. Further, the materials used are largely inert to common reagents associated with a chromatography column and may be supplied at a low cost and are easily constructed.

For instance, a graduated column may be modified so as to provide for a threadable connecter 28 along with the corresponding support ledge. The stainless steel matrix support may be supplied in any needed size to accommodate the column diameters.

The present resin support structure offers additional advantages over conventional supports. The resin support structure allows a back pressure to be applied against the column as a way of cleaning or reconstituting the column. Often, fine subparticles of the matrix gel may filter down so as to reduce the flow rate and elution or separation efficiency of the column. Applying a back pressure to the column will permit the desired column size gradient to be re-established. Conventional membranes, single-use resin support structures, steel wool plugs or ceramic frits used within the art will often rupture or lose their desired integrity if subjected to a back flushing or back pressure.

The ability to back flush the column allows continuation of a separation that would otherwise be terminated. A slight back pressure unclogs the matrix support mesh and allows the separation run to continue. The holder is easily washed and reused which shortens the preparation time of preparing a new column and avoids costs incurred by single use matrix holders. Further, the chromatography resin support structure may be modified as needed to fit any size diameter column. Likewise, the shape of the lower stainless steel cylinder wall may be tapered or configured as needed to mate appropriately with the inner glass column taper, ledge or other support structure. For instance, the tapered wall of the glass tube or volumetric cylinder may be engaged by a corresponding taper to the stainless steel cylinder wall.

While one or more preferred embodiments of the invention have been described above, it should be understood that any and all equivalent realizations of the present invention are included within the scope and spirit thereof. For example, the present invention may be embodied with a variety of different sized chromatography column. It should be understood by those of ordinary skill in this art that the present invention is not limited to these embodiments, since modifications can be made. Therefore, it is contemplated that any and all such embodiments are included in the present invention as may fall within the literal or equivalent scope of the following appended claims.

What is claimed is:

1. A resin support apparatus for a chromatography column comprising:
    a stainless steel cylinder having an outer diameter and an inner diameter, the outer diameter being greater than a height of the stainless steel cylinder, the cylinder defining a groove in an exterior wall of the stainless steel cylinder, the groove being substantially parallel to an upper and a lower rim of the stainless steel cylinder;
    an "O"-ring positioned within the groove, the "O"-ring having an outer diameter greater than the outer diameter of the stainless steel cylinder; and,
    a stainless steel mesh welded to an upper surface of the stainless steel cylinder and covering an opening defined by the stainless steel cylinder;
    wherein, when said stainless steel cylinder is placed within a receiving surface formed on an interior surface of a volumetric cylinder, the "O"-ring provides a fluid tight seal between the stainless steel cylinder and the inner wall of the volumetric cylinder, the stainless steel mesh providing a support platform adapted for receiving a supply of a chromatography matrix.

2. The apparatus according to claim 1 wherein said receiving surface further comprises a reduced diameter region of said volumetric cylinder.

3. The apparatus according to claim 1 wherein said receiving surface further comprises a ledge defined within an interior of said volumetric cylinder.

4. The apparatus according to claim 1 wherein said fluid-tight seal established by said "O" ring maintains the seal between said stainless steel cylinder and said interior wall of said volumetric cylinder when subjected to a back pressure.

5. A chromatography column comprising
    a stainless steel cylinder having an outer diameter and an inner diameter, the outer diameter being greater than a height of the stainless steel cylinder, the cylinder defining a groove in an exterior wall of the stainless steel cylinder, the groove being substantially parallel to an upper and a lower rim of the stainless steel cylinder;
    an "O"-ring positioned within the groove, the "O"-ring having an outer diameter greater than the outer diameter of the stainless steel cylinder; and,
    a stainless steel mesh welded to an upper surface of the stainless steel cylinder and covering an opening defined by the stainless steel cylinder;
    a volumetric cylinder having an interior surface, said interior surface further defining a receiving surface and engaging a bottom of said stainless steel cylinder, said "O" ring engaging a portion of said interior surface of said volumetric cylinder in a fluid-tight seal;
    wherein said stainless steel mesh and said stainless steel cylinder provide a support platform adapted for receiving a supply of a chromatography matrix.

6. The apparatus according to claim 5 wherein said receiving surface further comprises a reduced diameter region of said volumetric cylinder.

7. The apparatus according to claim 5 wherein said receiving surface further comprises a ledge defined within an interior of said volumetric cylinder.

8. The apparatus according to claim 5 wherein said fluid-tight seal established by said "O" ring maintains the seal between said stainless steel cylinder and said interior wall of said graduated cylinder when subjected to a back pressure.

* * * * *